United States Patent [19]
Takada

[11] Patent Number: 5,562,601
[45] Date of Patent: Oct. 8, 1996

[54] SELF-PROPELLED COLONOSCOPE

[76] Inventor: Masazumi Takada, 622-26, Takatsukashinden, Matsudo-shi, Chiba-ken, Japan

[21] Appl. No.: 409,864

[22] Filed: Mar. 24, 1995

[30] Foreign Application Priority Data

May 27, 1994 [JP] Japan .................................. 6-137917

[51] Int. Cl.⁶ .................................................. A61B 1/005
[52] U.S. Cl. .......................................... 600/114; 600/139
[58] Field of Search ........................ 15/104.33; 600/114, 600/120, 139, 152, 146, 149

[56] References Cited

U.S. PATENT DOCUMENTS

| | | | |
|---|---|---|---|
| 4,066,071 | 1/1978 | Nagel | 600/114 X |
| 4,176,662 | 12/1979 | Frazer | 600/114 |
| 4,561,427 | 12/1985 | Takada | 600/114 |
| 5,345,925 | 9/1994 | Allred, III et al. | 600/114 |

FOREIGN PATENT DOCUMENTS 1240760   8/1960   France .................................. 600/114

*Primary Examiner*—Richard J. Apley
*Assistant Examiner*—David R. Risley
*Attorney, Agent, or Firm*—Young & Thompson

[57] ABSTRACT

A self-propelled colonoscope comprises control part and an insertion tube including a distal part, a bending part, and a flexible part. The distal part is equipped with an image pickup element. Endless belts extend along the surfaces of the flexible part from a guide hole positioned at a distance of 3 to 10 cm from the distal end of the flexible part to the control part. The endless belts are driven by a driving mechanism situated in the control part. They are guided from the inner surface of the flexible part to the outer surface through the guide hole. The endless belts are held by guide hooks which are arranged on the outer surface of the flexible part. The colonoscope can be safely and rapidly inserted into the colon without causing pain to a patient thanks to the particular length of the endless belts. The endless belts are driven to guide the colonoscope by the effect of friction between the endless belts and the wall of the colon. The colonoscope does not cause abdominal pain nor accidents such as bleeding or perforation of the colon even in cases of adhesion of the colon from previous abdominal surgery, because it can be smoothly inserted without changing position and shape of the colon. When the endless belts slacken, their tension can be corrected with an adjustment mechanism connected to the colonoscope.

5 Claims, 6 Drawing Sheets

5,562,601

SELF-PROPELLED COLONOSCOPE

BACKGROUND OF THE INVENTION

1. Field of the Invention

The present invention relates to a novel endoscope. That is an endoscope which can be used for observation, photographing, biopsy and surgical operation of the colon without causing pain to a patient.

2. Description of the Related Art

Examination using an endoscope is widely used for observing, photographing a part of the examination, taking specimen from a lesion to ascertain if a tumor is malignant, observing other pathological and physiological conditions and processes, removing foreign body and performing endoscopic treatment. An endoscope is also useful in the examination of a colon. In the conventional method of examining a colon using an endoscope, the endoscope is manually inserted into the colon by pushing it with the hands, even though various other techniques can be applied. Therefore, it frequently occurs that a patient strongly complains of abdominal pain and distention because the colon is extended or excessively dilated and insertion of the endoscope into the colon must be stopped. Furthermore, it is not unusual for the colon to bleed and be accidentally perforated. In particular, these complaints frequently occur in cases of adhesion of the intestine from a previous abdominal operation. Therefore, a highly standardized technology is required for inserting an endoscope into a colon, and particularly for smoothly inserting the endoscope through the sigmoid colon and into the descending colon. Insertion of an endoscope through the splenic flexure, the transverse colon, the hepatic flexure or an adhesion part caused by previous operation is also accompanied with difficulty. Because of these reasons, a colonoscopy is only performed by a few doctors who are versed in the manipulation of a colonoscope. It is also considered that a patient has to endure some pain and discomfort.

SUMMARY OF THE INVENTION

An objective of the present invention therefore is to produce a colonoscope which can be rapidly, easily and safely inserted into a colon without giving pain to the patient.

As a result of extensive studies by the present inventor to achieve the above-mentioned object, it was discovered that such a colonoscope can be self-propelling when equipped with endless belts extending from the control part to a part ranging from a position of 3 to 10 cm from the distal end of the flexible part. The endless belts are driven by a driving mechanism equipped in the control part. A self-propelled colonoscope having such a structure may be smoothly inserted into the colon. The present invention was completed on the basis of this discovery.

Thus, the present invention provides a self-propelled colonoscope comprising a control part and an insertion section which comprises a distal part, a bending part and a flexible part. The distal part is equipped with an image pickup device such as a bundle of optical fibers which provides a return image guide, and a bundle of optical fibers which provide light guides for illumination. The flexible part is equipped with two or more endless belts. In other words, the self-propelled endoscope of the present invention can be automatically advanced in the colon by driving the endless belts. Each of the endless belts has a circular sectional shape and extends along the surfaces of the flexible part from an area ranging from a position of 3 to 10 cm from the distal end of the flexible part to the control part. Each endless belt is driven by a driving mechanism equipped in the control part, and is transferred from the inner surface of the flexible part to the outer surface through a guide hole formed at a position of 3 to 10 cm from the distal end of the flexible part. Each endless belt is held by guide hooks. These hooks are attached to the outer surface of the flexible part and have the shape of an arc covering more than one half of the circumferential length of the circular sectional shape of the endless belt. The length of an endless belt is equal to about 105% to 150% of what the length would be when the belt is fully tensioned and extends from the driving mechanism in the control part to the guide hole.

Other and further objects, features and advantages of the invention will appear more fully from the following description.

BRIEF DESCRIPTION OF THE DRAWINGS

The invention will be described with reference to the accompanying drawings, wherein.

Figure 1:
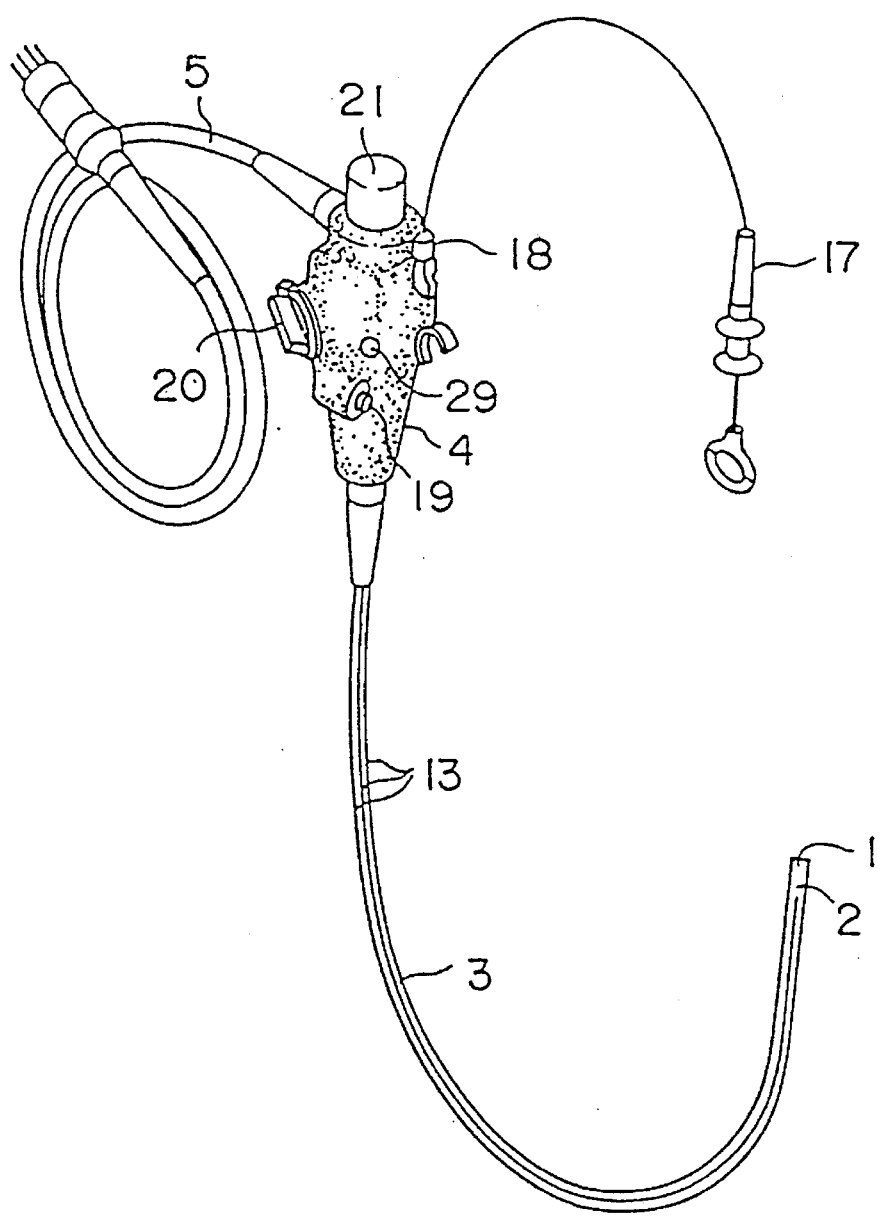
FIG. 1 shows a perspective view of the general arrangement of the endoscope of the present invention.

The numbers and characters in the figures have the meanings as listed in the following:

1. a distal part
2. a bending part
3. a flexible part
4. a control part
5. a connection tube
6. a window for receiving an image
7. a window for projecting light
8. an opening for suction and forceps
9. an air/water nozzle
10. an object lens
11. an image pickup device
12. a light guide
13. an endless belt
14. a guide hook
15. a guide pipe
16. a guide hole
17. forceps
18. an opening for insertion of forceps
19. an air/water control valve
20. a control knob
21. a driving mechanism
22. a guide roller
23. a guide roller 24. a row of gears
25. a motor
26. the inside of the flexible part
27. a return image guide
28. an eyepiece section
29. a suction control valve

DETAILED DESCRIPTION OF THE INVENTION

The present invention will now be described in detail with reference to the following drawings.

Figure 2:
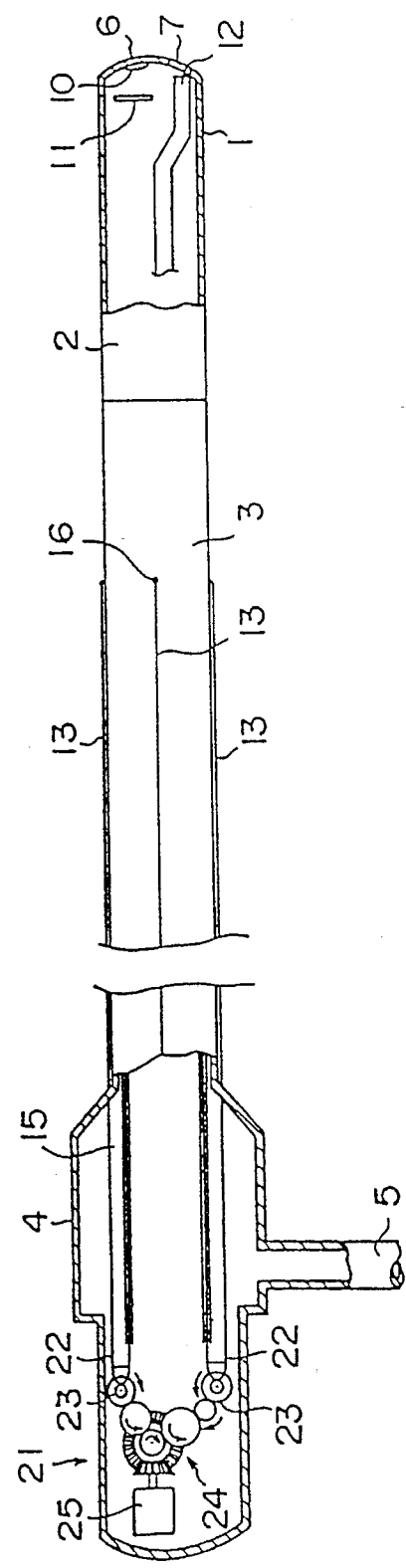
FIG. 2 shows a sectional view of a part of an endoscope of the present invention.

FIG. 1 shows a perspective view of the general arrangement of the endoscope of the present invention. FIG. 2 shows a sectional view of a part of an endoscope of the present invention. The colonoscope of the present invention comprises a distal part 1, a bending part 2, a flexible part 3, and a control part 4 attached to the base end of the flexible part. The length of the distal part is 0.9 cm. The length of the bending part is 10 cm. The length of the flexible part is about 157 cm.

In the colonoscope of the present invention, the bending part 2 is formed in such a manner that it can be bent in any direction by manipulation of a control knob 20 in the control part 4.

Figure 3:
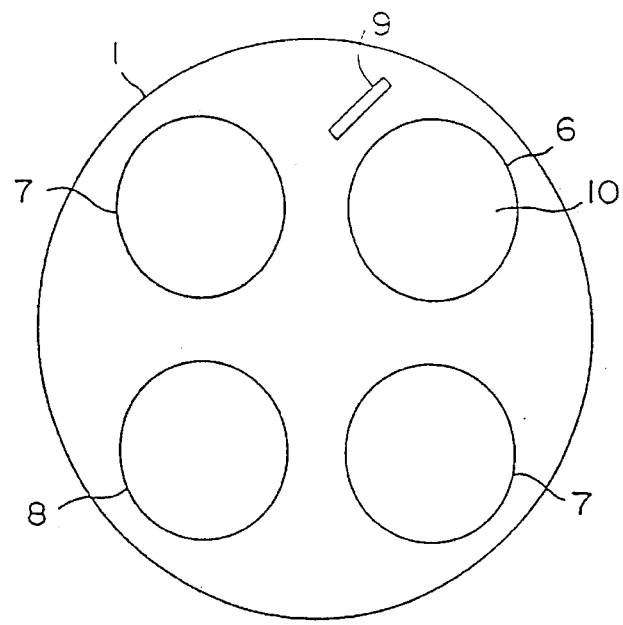
FIG. 3 shows a front view of the distal part.

FIG. 3 shows a front view of the distal part. In the distal part, a window 6 fitted with a transparent material receives the image. Two windows 7 fitted with a transparent material project light, and an opening 8 for suction and forceps and an air/water nozzle 9 are also provided in the distal part. An object lens 10 and an image pickup device 11 are positioned inside the distal part 1 and face the image receiving window 6. Light guides 12 are also placed inside the distal part 1 at positions facing the light projecting windows 7. As the image pickup device, a charge combining device CCD may for example be used.

Figure 4:
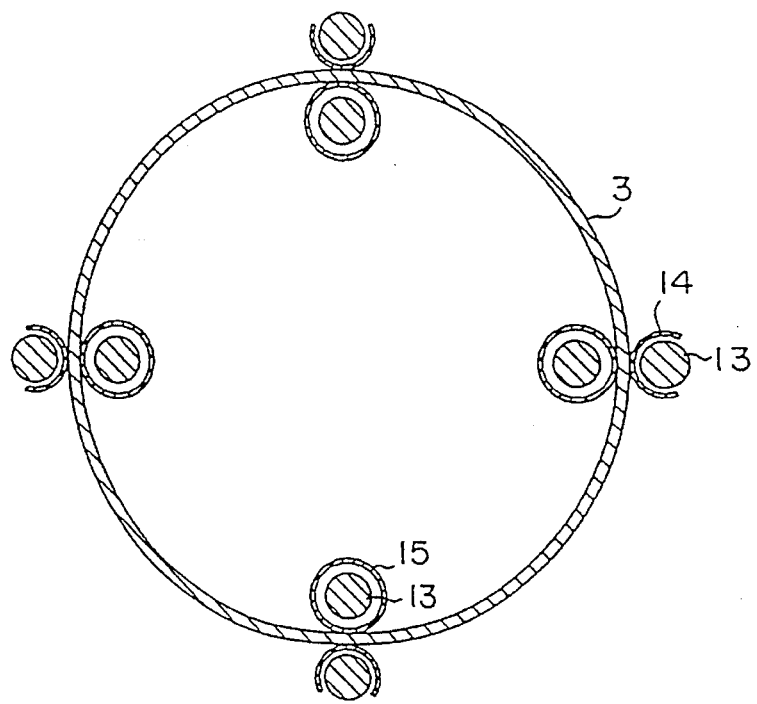
FIG. 4 shows a section view of the flexible part.

FIG. 4 shows a sectional view of the flexible part 3 of the colonoscope of the present invention. The flexible part 3 is equipped with two or more endless belts 13 along surfaces in the longitudinal direction of the endoscope. When the flexible part is equipped with 3 or 4 endless belts, the endoscope is generally provided with sufficient self-propelling property. When the flexible part is equipped with a single endless belt, the endoscope is not provided with the smooth self-propelling property. When the flexible part is equipped with 5 or more endless belts, it has been found that such a number of endless belts is more than necessary for providing the self-propelling property, and such an increased number of endless belts causes an increase in the diameter of the flexible part and of the control part. Thus, a flexible part equipped with a single endless belt or 5 or more endless belts is not preferred. The endless belt is held by guide hooks 14 arranged on the outer surface of the flexible part. Each guide hook has a diameter slightly larger than the diameter of the endless belt and has a shape of an arc which is greater than 180°, thereby covering more than one half of the circumferential length of the circular sectional shape of the endless belt. When the guide hook has a shape of an arc which is equal to or smaller than 180°, thereby covering one half or less of the circumferential length of the circular sectional shape of the endless belt, the guide hook cannot hold the endless belt. The guide hooks are arranged on the outer surface of the flexible part with a distance ranging from 0 to 8 cm, preferably 0 to 6 cm, from each other in the longitudinal direction of the flexible part.

Inside the flexible part 26 of the colonoscope are disposed, guide pipes 15 for the endless belts, a lead wire for transmitting image signals received at the image pickup device 11 to an outside apparatus, such as a monitoring apparatus or a bundle of optical fibers for the return image guide, a bundle of optical fibers for the light guide, a tube for supplying air and water, a guide tube for suction and forceps, mechanisms used for the operation and other elements as needed. These mechanisms are omitted in FIG. 4.

Figure 5:
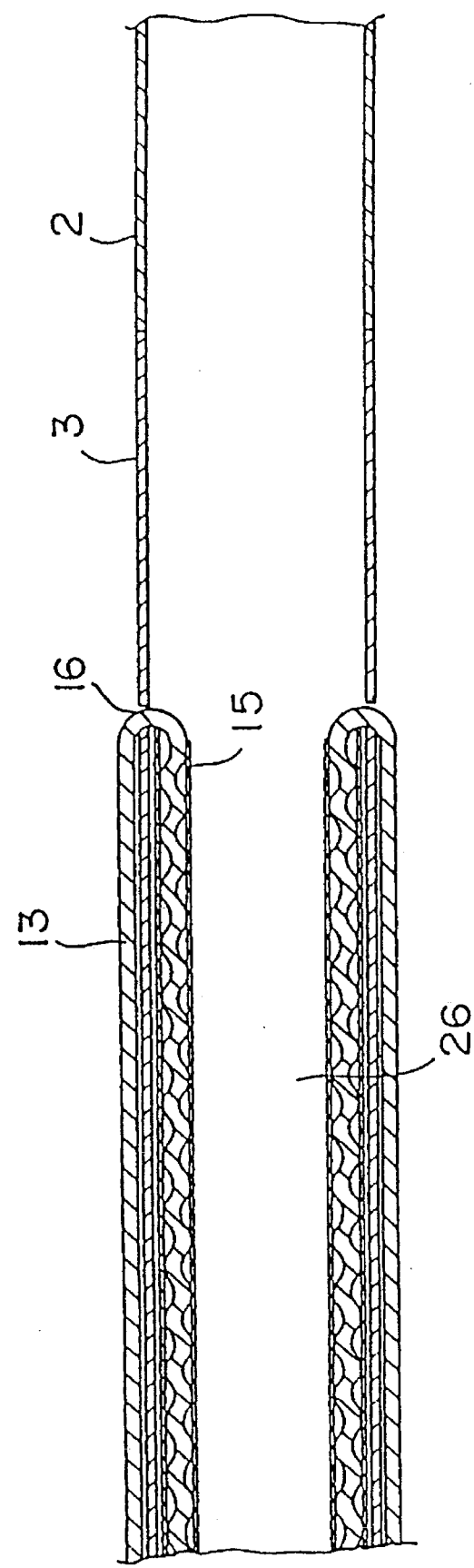
FIG. 5 shows a section view of the part around the distal end of the flexible part.
Figure 6:
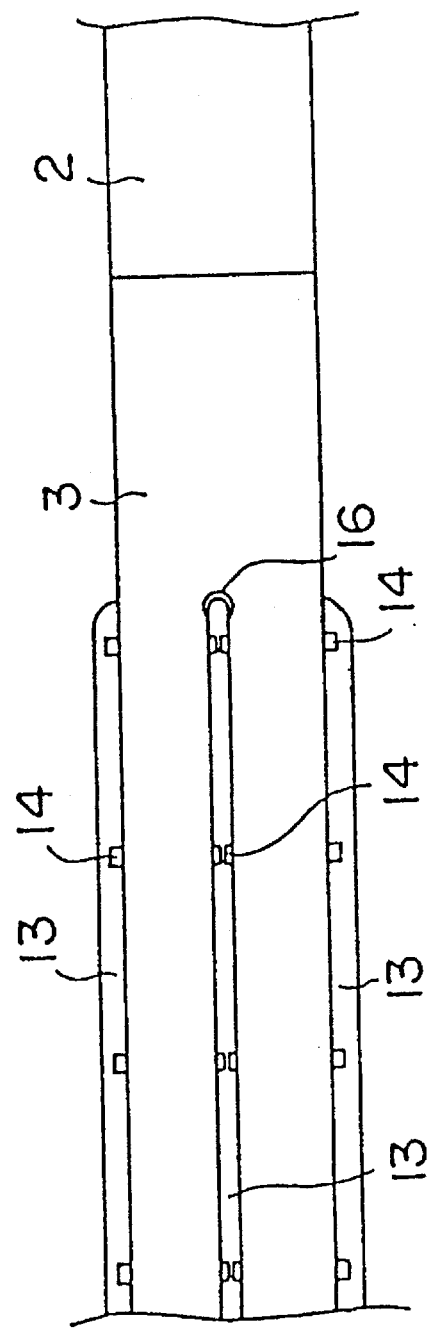
FIG. 6 shows a plane view of the part around the distal end of the flexible part.

FIG. 5 shows a sectional view of the part around the distal end of the flexible part. FIG. 6 shows a plane view of the part around the distal end of the flexible part. The endless belt which travels within a guide pipe 15 inside of the flexible part toward the distal end of the flexible part is guided to the outside of the flexible part via a guide hole 16 formed at a position ranging from 3 to 10 cm from the distal end of the flexible part. When the guide hole is formed at a position of less than 3 cm from the distal end of the flexible part, the flexible part tends to be easily damaged. When the guide hole is formed at a position of more than 10 cm from the distal end of the flexible part, the self-propelling property is inferior during the initial period, after insertion of the endoscope into the colon. Thus, a position of less than 3 cm or more than 10 cm from the distal end of the flexible part is not preferred.

In the colonoscope of the present invention, the endless belt emerges to the outside of the flexible part through the guide hole is returned toward the control part by a driving mechanism disposed in the control part. The endless belts disposed on the surface of the flexible part of this particular colonoscope touch the wall of the colon. By the movement of the endless belts, the colonoscope moves toward the inside of the colon. It is not necessary to push manually the endoscope into the colon. The guide hole is made fluid-tight with an 0-ring or a bearing to prevent penetration of foreign bodies from the colon into the inside of the flexible part. When an 0-ring is used, one made of a material having a small friction resistance, such as polytetrafluoroethylene, is suitable. A bearing made of plastics, such as nylon, or of metal, such as stainless steel, can be used when a bearing is used. The guide pipe 15 is required to have a diameter larger than that of the endless belt because the endless belt is relaxed in the guide pipe.

In this colonoscope, the length of the endless belt is equal to 105 to 150% of an imaginary belt fully tensioned and extending from the driving mechanism in the control part to the guide hole positioned at a distance of 3 to 10 cm from the distal end of the flexible part when the flexible part is kept straight. By providing an endless belt with a length equal to 105 to 150% of an imaginary fully tensioned endless belt extending between the guide hole and the driving mechanism, the endless belt can effectively follow the bending of the flexible part, even when the flexible part of the colonoscope passes through a bent part like the sigmoid colon. Thus, the colonoscope can be inserted inside the colon with stability. The material of the endless belt is not particularly critical, but carbon fiber is preferable.

In the colonoscope of the present invention, an endless belt having a diameter of 1 to 3 mm and a flexible part having a diameter of 10 to 30 mm are preferably used.

On the outside of the control part 4 of this colonoscope are disposed several elements. These include a flexible connection tube 5 for leading various kinds of wire, the bundle of optical fibers for the light guides 12 and various kinds of tubing passing through the inside of the flexible part 3 to the outside, a forceps insertion opening 18 for insertion of protruding forceps 17 from the opening 8 through a suction and forceps guide tube in an insertion tube, a suction control valve 29, an air/water control valve 19 and a control knob 20 for bending the bending part 2 in any direction. On the inside of the control part 4, there is provided a driving mechanism 21 for driving the endless belt 13. The driving mechanism 21 is comprised of a pair of guide rollers, 22 and 23, holding the endless belt between them and a motor 25 rotating one of the guide rollers 23 through a row of gears 24 comprised of spur wheels and bevel gears.

In using the colonoscope of the present invention the distal part 1 is manually inserted directly from the anus to the upper end of the rectum. Then, the motor 25 is rotated to drive the guide roller 23 which in turn drives the endless belt 13. Since the endless belts 13 have a circular sectional shape and are placed along the outer surface of the flexible part, they are in contact with the wall of the rectum. The flexible part is transferred further within the colon by the friction between the endless belts and the wall of the colon. Thereafter, the distal part, the bending part and the flexible part pass through the sigmoid colon and are self-propelled to reach the deepest point of the colon by the effect of friction between the walls of the colon and the rectum and the endless belts. Thus, the distal end of the flexible part is guided along the wall of the colon by the driving of the endless belts, even at the bent portions of the colon. The distal part can be inserted into the desired part in the colon without causing pain to the patient. The direction of the distal part can be adjusted to any direction using the control knob 20. It is not at all necessary to push manually the endoscope into the colon.

In the colonoscope of the present invention, the endless belts are equipped along substantially the entire length of the outer surface of the flexible part. The longer the portion of the flexible part inserted into the colon, the larger the area of contact between the endless belts and the wall of the colon. Thus, the distal end can be safely inserted to a desired deep part in the colon without causing excessive friction on particular parts of the wall of the colon. Furthermore, the endless belts are firmly held to the flexible part during bending of the flexible part caused by bending of the colon, and are kept in place along the wall of the colon thanks to the guide hooks. Therefore, injury of the wall of the colon will be prevented and advance of the colonoscope in the colon will not be impaired.

Figure 7:
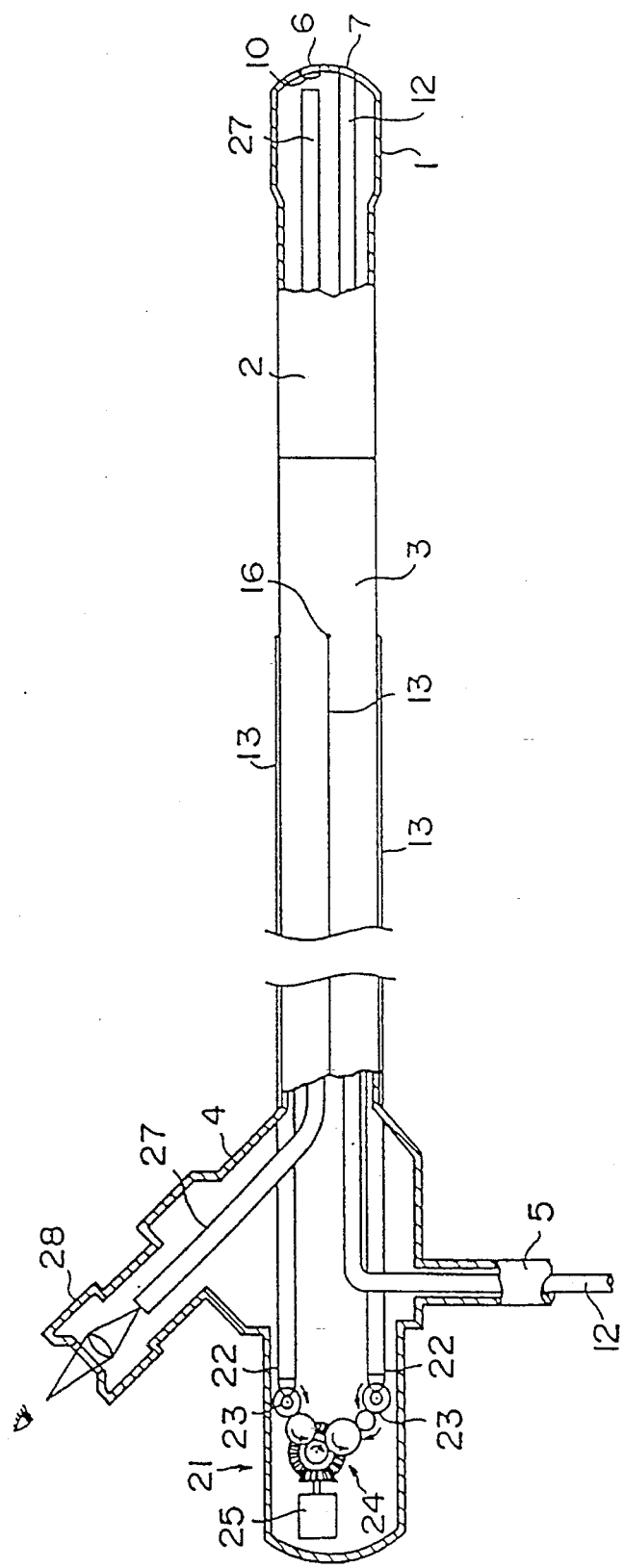
FIG. 7 shows a section view of a part of the endoscope used as a fiber scope.

The colonoscope of the present invention can be used in both electronic scopes and fiber scopes. FIG. 7 shows a sectional view of a part of an endoscope used as a fiber scope according to the present invention. In such a colonoscope, the image picked up through the window for receiving an image at the distal part can be directly observed at the eyepiece section 28 through the bundle of optical fibers of the return image guide 27.

To summarize the advantages of the present invention, the colonoscope of the present invention can be safely and rapidly inserted into the colon without causing pain to a patient even when the flexible part is bent, because the endless belts provided along the outer surface of the flexible part have a particular length, and are guidedly driven by the effect of friction between the endless belts and the wall of the colon.

While the invention has been depicted and described with reference to preferred embodiments thereof, it will be understood by those skilled in the art that the foregoing and other changes in form and details can be made therein without departing from the spirit and scope of the invention.

I claim:

1. A self-propelled colonoscope comprising: a control part, and an insertion section which comprises a distal part, a bending part, and a flexible part having a throughbore and an outer surface comprising a plurality of guide hooks, each guide hook having an arc shape which is greater than 180°, said bending part extending between said flexible part and said distal part, and said flexible part extending between said control part and said bending part, drive means located at said control part for driving at least two endless belts each of which is circular in cross section, each endless belt extending between said control part and a respective guide hole of a plurality of guide holes, each guide hole extending through said flexible part from said outer surface to said throughbore, each guide hole being positioned 3 to 10 cm from an interface of said bending part and said flexible part, each endless belt extending within said flexible part in said throughbore from said control part to a respective guide hole and then extending external of said flexible part along said outer surface through respective guide hooks of said plurality of guide hooks from a respective guide hole back to said control part, the length of each endless belt being equal to about 105% to 150% of an imaginary endless belt fully tensioned and extending from said control part to a respective guide hole.

2. A self-propelled colonoscope according to claim 1, wherein the plurality of guide hooks are arranged on the outer surface of the flexible part at a distance ranging from 0 to 8 cm from each other in a longitudinal direction of the flexible part.

3. A self-propelled colonoscope according to claim 1, wherein the number of endless belts ranges from 2 to 4.

4. A self-propelled colonoscope according to claim 1, wherein the control part includes control knob means for bending the bending part in any desired direction.

5. A self-propelled colonoscope according to claim 1, wherein each endless belt travels within a respective guide pipe, within the throughbore of the flexible part.

* * * * *